(12) United States Patent
Schroeder et al.

(10) Patent No.: US 9,655,515 B2
(45) Date of Patent: May 23, 2017

(54) METHOD OF PRECISION EYE-TRACKING THROUGH USE OF IRIS EDGE BASED LANDMARKS IN EYE GEOMETRY

(75) Inventors: John Howison Schroeder, Pittsburgh, PA (US); Alexander D. Kiderman, Pittsburgh, PA (US)

(73) Assignee: NEURO KINETICS, Pittsburgh, PA (US)

( * ) Notice: Subject to any disclaimer, the term of this patent is extended or adjusted under 35 U.S.C. 154(b) by 2266 days.

(21) Appl. No.: 12/420,111

(22) Filed: Apr. 8, 2009

(65) Prior Publication Data

US 2010/0092049 A1 Apr. 15, 2010

Related U.S. Application Data

(60) Provisional application No. 61/043,349, filed on Apr. 8, 2008.

(51) Int. Cl.
*G06K 9/00* (2006.01)
*A61B 3/113* (2006.01)

(52) U.S. Cl.
CPC .......... *A61B 3/113* (2013.01); *G06K 9/00604* (2013.01)

(58) Field of Classification Search
CPC ....... A61B 3/113; A61B 3/0066; A61B 3/145; A61B 3/00; A61F 2009/00846; A61F 2009/00876; G06F 3/013; G06K 9/00597; G06K 9/0061; G06K 9/52; G06T 2207/30041; G06T 7/0083; H04N 13/0484
USPC .......................................... 382/128; 351/210
See application file for complete search history.

(56) References Cited

U.S. PATENT DOCUMENTS

| 3,612,642 A | 10/1971 | Dostal |
| 4,006,974 A | 2/1977 | Resnick |
| 4,084,182 A | 4/1978 | Maiman |
| 4,309,608 A | 1/1982 | Adamson |
| 4,320,768 A | 3/1982 | Ledley |
| 4,474,186 A | 10/1984 | Ledley |
| 4,572,199 A | 2/1986 | LaCourse |

(Continued)

FOREIGN PATENT DOCUMENTS

JP 11/184621 7/1999

OTHER PUBLICATIONS

Maria Fontanazza, Device Eases Diagnosis of Concussions and Other Cognitive Conditions, http://www.devicelink.com/mddi/archive/05/07/010.html.

(Continued)

*Primary Examiner* — Kim Vu
*Assistant Examiner* — Michael Vanchy, Jr.
(74) *Attorney, Agent, or Firm* — Blynn L. Shideler; Krisanne Shideler; BLK Law Group

(57) ABSTRACT

In the field of eye tracking, greater accuracy or resolution in monitoring movement of the eye can be gained by digitizing the eye, and tracking the movement of a landmark with fixed size and a fixed location relative to the eye's local coordinate system. The edge of the iris can be used as such a fixed landmark. Through the location and or establishment of at least a portion of the outer edge of the iris and/or an iris center point, both large and small scale eye movements, including but not limited to micro-tremors, can be traced with a higher degree of accuracy. This will aid in the diagnosis of diseases, assessing state of consciousness, and defining brainstem death.

18 Claims, 1 Drawing Sheet

(56) References Cited

U.S. PATENT DOCUMENTS

| | | | |
|---|---|---|---|
| 4,836,219 A | 6/1989 | Hobson | |
| 4,852,988 A | 8/1989 | Velez et al. | |
| 4,863,259 A | 9/1989 | Schneider | |
| 5,070,883 A | 12/1991 | Kasahara | |
| 5,098,426 A | 3/1992 | Sklar | |
| 5,130,838 A | 7/1992 | Tanaka | |
| 5,252,999 A | 10/1993 | Sukigara | |
| 5,304,112 A | 4/1994 | Mrklas | |
| 5,305,746 A | 4/1994 | Fendrock | |
| 5,320,109 A | 6/1994 | Chamoun | |
| 5,345,281 A | 9/1994 | Taboada | |
| 5,365,941 A | 11/1994 | Yoshimatsu | |
| 5,368,041 A | 11/1994 | Shambroom | |
| 5,381,804 A | 1/1995 | Shambroom | |
| 5,410,376 A | 4/1995 | Cornsweet | |
| 5,458,117 A | 10/1995 | Chamoun | |
| 5,481,622 A | 1/1996 | Gerhardt | |
| 5,491,492 A | 2/1996 | Knapp | |
| 5,652,756 A | 7/1997 | Stultz | |
| 5,687,020 A | 11/1997 | Park | |
| 5,704,369 A | 1/1998 | Scinto | |
| 5,714,967 A | 2/1998 | Okamura | |
| 5,792,069 A | 8/1998 | Greenwald | |
| 5,813,404 A | 9/1998 | Devlin | |
| 5,821,521 A | 10/1998 | Bridgelall | |
| 5,838,420 A | 11/1998 | Donaldson | |
| 5,892,566 A | 4/1999 | Bullwinkel | |
| 5,942,954 A | 8/1999 | Galiana | |
| 5,943,116 A | 8/1999 | Zeimer | |
| 5,963,300 A | 10/1999 | Horwitz | |
| 5,980,513 A | 11/1999 | Frey | |
| 5,983,128 A | 11/1999 | Baudonniere | |
| 6,003,991 A | 12/1999 | Viirre | |
| 6,024,707 A | 2/2000 | Scinto | |
| 6,032,064 A | 2/2000 | Devlin | |
| 6,032,072 A | 2/2000 | Greenwald | |
| 6,033,073 A | 3/2000 | Potapova | |
| 6,077,237 A | 6/2000 | Campbell | |
| 6,089,716 A | 7/2000 | Lashkari | |
| 6,090,051 A | 7/2000 | Marshall | |
| 6,099,124 A | 8/2000 | Hidaji | |
| 6,099,522 A * | 8/2000 | Knopp et al. | 606/10 |
| 6,113,237 A | 9/2000 | Ober | |
| 6,120,461 A | 9/2000 | Smyth | |
| 6,162,186 A | 12/2000 | Scinto | |
| 6,213,943 B1 | 4/2001 | Abreu | |
| 6,231,187 B1 | 5/2001 | Munoz | |
| 6,247,813 B1 | 6/2001 | Kim | |
| 6,271,915 B1 | 8/2001 | Frey | |
| 6,275,718 B1 | 8/2001 | Lempert | |
| 6,299,307 B1 * | 10/2001 | Oltean et al. | 351/210 |
| 6,299,308 B1 | 10/2001 | Voronka | |
| 6,367,932 B1 | 4/2002 | Donaldson | |
| 6,402,320 B1 | 6/2002 | Borchert | |
| 6,456,261 B1 | 9/2002 | Zhang | |
| 6,459,446 B1 | 10/2002 | Harman | |
| 6,467,905 B1 | 10/2002 | Stahl | |
| 6,524,581 B1 | 2/2003 | Adamis | |
| 6,542,081 B2 | 4/2003 | Torch | |
| 6,551,575 B1 | 4/2003 | Greenspan | |
| 6,568,808 B2 | 5/2003 | Campin | |
| 6,574,352 B1 | 6/2003 | Skolmoski | |
| 6,609,523 B1 | 8/2003 | Anthony | |
| 6,629,935 B1 | 10/2003 | Miller | |
| 6,631,989 B2 | 10/2003 | Odom | |
| 6,634,749 B1 | 10/2003 | Morrison | |
| 6,637,883 B1 | 10/2003 | Tengshe | |
| 6,652,458 B2 | 11/2003 | Blazey | |
| 6,659,611 B2 | 12/2003 | Amir | |
| 6,669,341 B2 | 12/2003 | Wirth | |
| 6,697,894 B1 | 2/2004 | Mitchell | |
| 6,748,275 B2 | 6/2004 | Lattner | |
| 6,796,947 B2 | 9/2004 | Watt | |
| 6,800,062 B2 | 10/2004 | Epley | |
| RE38,668 E | 12/2004 | Edwards | |
| 6,943,754 B2 | 9/2005 | Aughey | |
| 7,019,778 B1 | 3/2006 | Prabhu | |
| 7,448,751 B2 | 11/2008 | Kiderman | |
| 7,465,050 B2 | 12/2008 | Migliaccio et al. | |
| 7,520,614 B2 | 4/2009 | Joos et al. | |
| 7,665,845 B2 | 2/2010 | Kiderman et al. | |
| 2002/0027779 A1 | 3/2002 | Cassarly | |
| 2002/0085174 A1 | 7/2002 | Bolger | |
| 2002/0171805 A1 | 11/2002 | Odom | |
| 2002/0175880 A1 | 11/2002 | Melville | |
| 2003/0028081 A1 | 2/2003 | Blazey | |
| 2004/0181168 A1 | 9/2004 | Plant | |
| 2005/0024586 A1 | 2/2005 | Teiwes | |
| 2005/0079636 A1 | 4/2005 | White | |
| 2005/0099601 A1 | 5/2005 | MacDougall | |
| 2005/0101877 A1 | 5/2005 | Miller | |
| 2005/0110950 A1 | 5/2005 | Thorpe | |
| 2005/0216243 A1 | 9/2005 | Graham | |
| 2005/0278004 A1 * | 12/2005 | Steinert et al. | 607/89 |
| 2006/0039583 A1 * | 2/2006 | Bickert et al. | 382/103 |
| 2006/0098087 A1 | 5/2006 | Brandt | |
| 2006/0167670 A1 * | 7/2006 | Deering | 703/11 |
| 2006/0235331 A1 | 10/2006 | Kiderman | |
| 2007/0132841 A1 | 6/2007 | MacDougall | |
| 2007/0140531 A1 * | 6/2007 | Hamza | 382/117 |
| 2008/0049186 A1 | 2/2008 | MacDougall | |
| 2008/0053253 A1 | 3/2008 | Moore et al. | |
| 2008/0151192 A1 | 6/2008 | Wood | |
| 2008/0273084 A1 | 11/2008 | MacDougall | |
| 2008/0278685 A1 | 11/2008 | MacDougall | |
| 2009/0198148 A1 * | 8/2009 | Lonky | 600/558 |

OTHER PUBLICATIONS

Jason S. Babcock, Jeff B. Pelz, Building a lightweight eyetracker, http://www.cis.rit.edu/people/faculty/pelz/publications/ETRA04_babcock_pelz.pdf, 2004.

D. Zhu et al., Computer Methods and Programs in Biomedicine 59 (1999), pp. 146-157.

Hamish G. MacDougall, Applicants description of Prior Art Systems, Applicants internal memo regarding Prior Art.

Moore et al., A geometric Basis for Measurement of Three-Dimensional Eye Position Using Image Processing, pp. 445-459, Vision Res. vol. 36.

* cited by examiner

METHOD OF PRECISION EYE-TRACKING THROUGH USE OF IRIS EDGE BASED LANDMARKS IN EYE GEOMETRY

RELATED APPLICATIONS

This application claims the benefit of U.S. Provisional Patent Application No. 61/043,349, filed Apr. 8, 2008, entitled "Method of Precision Eye-tracking Through Use of Iris Edge Based Landmarks in Eye Geometry"

BACKGROUND OF THE INVENTION

1. Field of the Invention

The present invention pertains generally to eye tracking technologies, and more particularly to precision eye tracking through use of relative iris edge based landmarks in eye geometry.

2. Background Information

In addition to the eyes being the "gateway to the soul" (Herman Melville), a subject's eyes are an incredibly sensitive bio-indicator that can be utilized for many functions.

Eye movement is the voluntary or involuntary movement of the eyes, helping in acquiring, fixating and tracking visual stimuli. In addition, rapid eye movement (REM) occurs during REM sleep.

"Eye tracking is the process of measuring either the point of gaze ("where we are looking") or the motion of an eye relative to the head. An eye tracker is a device for measuring eye positions and eye movements. Eye trackers are used in a wide array of applications including research in numerous fields, medical diagnosis, psychology, in cognitive linguistics and even in advertising and product design. There are a number of methods for measuring eye movements. The most popular variant is a non-invasive technique that uses video images from which the eye position is extracted. Other methods use search coils or are based on the electro-oculogram. The non-invasive technique for recording eye position relative to the head using a camera to record eye position relative to the head is also known as video oculography or VOG. VOG systems are used by Vestibular Researchers, Ophthalmologist, Otolaryngologists, Physical Therapists, Neurologists, Audiologists, Balance Clinicians, Neurophysiologists, Physiologists, Neuroscientists, Occupational Therapists, and others.

The most widely used current designs are video-based eye trackers. A camera focuses on one or both eyes and records their movement as the subject viewer will often look at some kind of stimulus. Most modern eye-trackers use contrast to locate the center of the pupil. Image processing software is utilized to interpret the images to provide objective data of eye position. This type of image processing software is described in "A GEOMETRIC BASIS FOR MEASUREMENT OF THREE-DIMENSIONAL EYE POSITION USING IMAGE PROCESSING" Vision Res. Volume 36. No. 3, Moore et al., pp 445-459, 1996, which is incorporated herein by reference. In general, most eye tracking devices digitize an image of the, define the pupil using the high contrast difference between the pupil and the rest of the eye, and then define the center of the pupil by approximating a circle of the same size or calculating the centroid of the pupil itself. For relatively large-scale eye movements, such as saccades and nystagmus, this method is appropriate despite of the fact that the pupil changes in size and, to a lesser degree, shape.

Accurate eye position recording and monitoring in three dimensions (3D-yaw, pitch and torsion rotation about line of sight) is a significant clinical diagnostic tool in the field of vestibular disorders such as vertigo and other neurological disorders.

There is a need for greater precision in eye tracking systems.

SUMMARY OF THE INVENTION

In the field of eye tracking, greater accuracy or resolution in monitoring the movement of the eye can be gained by digitizing the eye, and tracking the movement of a landmark with fixed size and a fixed location relative to the eye's local coordinate system. At least a portion of the edge of the iris can be used as such a fixed landmark, or simply landmark. Further, by defining at least a portion of the edge of the iris, possibly even calculating its center (or other fixed landmark relative to the calculated iris edge), and tracking a portion of the edge and/or the center over time, both large and small scale eye movements, including but not limited to microtremors, can be traced with a higher degree of accuracy. This will aid in the diagnosis of diseases, assessing state of consciousness, and defining brainstem death.

These and other objects of the present invention will be clarified in the following description which is taken together with the attached figures in which like reference numerals represent like elements throughout.

DETAILED DESCRIPTION OF THE INVENTION

Figure 1:
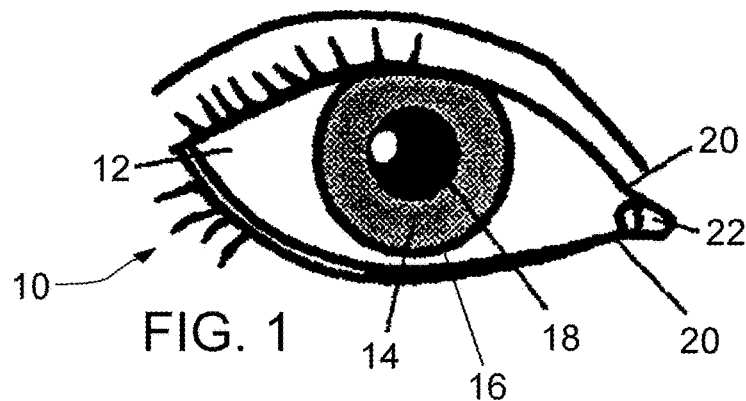
FIG. 1 is a schematic view of an image of a subject's eye.
Figure 2:
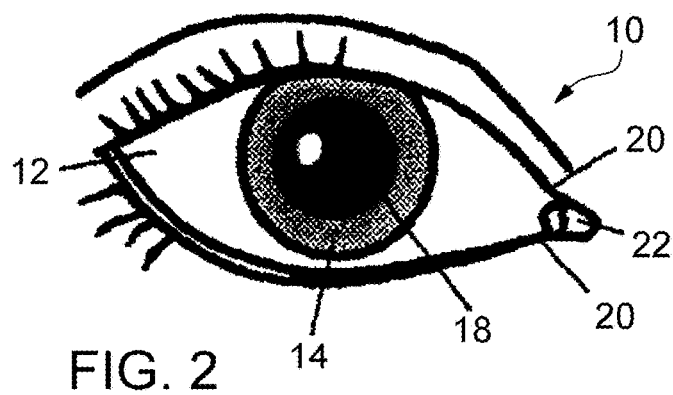
FIG. 2 is a schematic view of an image of the subject's eye of FIG. 1 illustrating a representative change in pupil size and shape.

A complete understanding of the invention will be obtained from the following description when taken in connection with the accompanying drawing figures, wherein like reference characters identify like parts throughout. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. FIGS. 1 and 2 are schematic views of an image of a subject's eye 10, including the sclera 12, iris 14 with iris edge 16, pupil 18, tear ducts 20 and eye muscle 22.

As discussed above, most eye tracking devices digitize an image of the, define the pupil 18 using the high contrast difference between the pupil 18 and the rest of the eye 10, and then define the center of the pupil 18 by approximating a circle of the same size or calculating the centroid of the pupil 18 itself. For relatively large-scale eye movements, such as saccades and nystagmus, this method is appropriate despite of the fact that the pupil 18 changes in size and, to a lesser degree, shape. However, greater accuracy or even resolution in monitoring the movement of the eye 10 can be gained by digitizing the eye 10, and tracking the movement of a landmark with fixed size and a fixed location relative to the eye's local coordinate system. The edge of the iris 16 can be used as such a fixed landmark. The present invention provides that by defining or establishing at least a portion of the outer edge 16 of the iris 14 both large and small scale eye movements, including but not limited to micro-tremors, can be traced with a higher degree of accuracy. This will aid in the diagnosis of diseases, assessing state of consciousness, and defining brainstem death.

The term landmark within the meaning of the present application will reference a perceptible or visible artifact that is fixed relative to the local co-ordinate system of the eye 10. The eye 10 defines a local co-ordinate system, often represented with an axis "through" the center of the pupil 18 generally along a gaze path and two perpendicular axes thereto. It does not matter where the local co-ordinate system is established within the eye 10, rather that the artifact is fixed in such a local system such that it is a landmark or a fixed landmark. In other words the landmarks will move with the eye 10.

The concepts of the present invention can be explained in connection with FIGS. 1-2. In these figures the wide variation in the pupil 18 size (and shape) will illustrate that the pupil 18 monitoring methods results in a certain amount of error. The pupil center is established typically by approximating the shape of the pupil 18 as a circle, and, the center of the circle (the assumed center of the eye 10), in theory remains unchanged as the circle expands in diameter due to changes in pupil 18 diameter. However these are merely approximations that lead to noise in the system that prevents the system from identifying small eye movements, such as micro-tremors.

Figure 3:
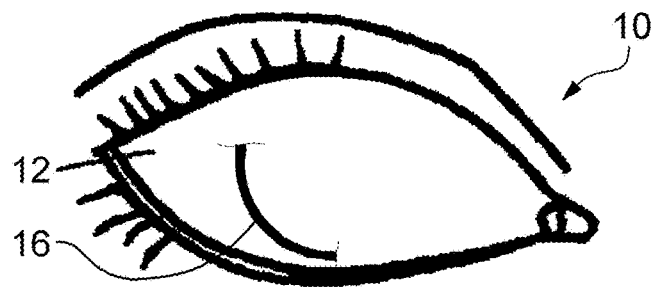
FIG. 3 is a schematic representation of a relative location marker in accordance with one aspect of the present invention.

The present invention utilized at least a portion of the outer edge 16 of the iris 14 as a landmark for tracking eye movement. As shown in FIG. 3, the iris outer segment 16, namely the lower outer quadrant, can be used as a landmark and this segment 16 viewed to determine eye 10 movement. The representation in FIG. 3 illustrates that the eye 10 position has not moved from FIG. 1-2 even though the pupil 18 diameter and shape has changed between these two representations.

The image processing for establishing the outer iris edge 16 is substantially the same as for pupil 18 edge detection, and is the same as general edge detection in image processing as known in the art. The term iris edge 16 is intended to be broad enough to cover various formulations of finding such an image border. For example, in some edge recognition programs, an image will convert the color of different pixels to ranges or even to merely 0 and 1 depending upon a fixed threshold. In order to distinguish between noise and other eye artifacts (eye vessel), the edge detection algorithm may select find the first 1 in a row and verify that the next 2-5 pixels are also 1 before calculating that it is an edge, or may look at the surrounding X pixel values before calculating that the iris edge has been found. The term iris edge 16 will define the edge 16 of the iris 14 within the scope of image edge detection algorithms.

The present invention contemplates detecting the outer iris edge 16 and utilizing at least a portion of this as a landmark for eye tracking. The length of the segment 16 that is utilized can be varied and the quadrant shape is merely an illustration. In some applications a single or distinct iris edge 16 point will be a sufficient landmark to track. A plurality of edge points at different locations or of edge segments 16 at different locations could also be utilized as eye 10 landmarks within the scope of the present invention.

A further aspect of the present invention is to utilize the iris edge 16 to define a center of the iris 14 and to use the center of the iris 14 as an eye tracking landmark.

The center of the iris landmark would be at the centroid X of the iris area. The centroid of an area is very similar to the center of mass of a body. The centroid is calculated using only the geometry of the figure. The general function for calculating the centroid of a geometrically complex cross section is most easily applied when the figure is divided into known simple geometries and then applying the formula:

$$\bar{x} = \frac{\sum \bar{x_i} A_i}{\sum A_i}$$

$$\bar{y} = \frac{\sum \bar{y_i} A_i}{\sum A_i}$$

The distance from the y-axis to the centroid is $\bar{x}$
The distance from the x-axis to the centroid is $\bar{y}$
The coordinates of the centroid are $(\bar{x}, \bar{y})$.

Figure 4:
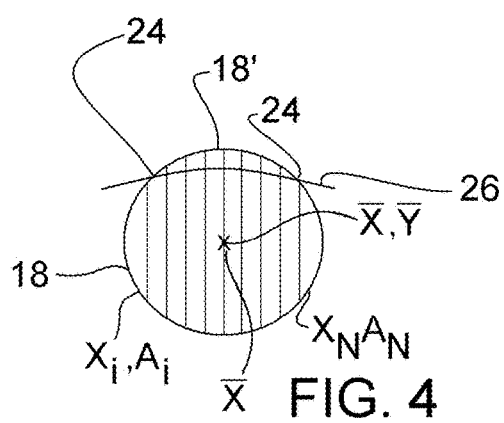
FIG. 4 is a schematic representation of portions of calculating a geometric center of an iris in accordance with one aspect of the present invention.

This calculation of a centroid X of the iris 14 is represented in FIG. 4 in schematic fashion. One further aspect is that to calculate the iris centroid X the full shape of the iris 14 must be used. Thus the present invention contemplates looking for discontinuities 24 along the originally presumed iris edge 16, which could be indicative of the lid 26 cutting across the iris 14 portion. In this case the full iris 14 will need to be approximated with an iris edge approximation 18' between the points of discontinuity 24 based upon the general shape of the remaining iris 14 portions. The methods of interpolating between the discontinuities 24 based upon the remaining portions 16 of the iris edge are believed to be well understood.

A further iris 14 based landmark would be a centroid of an iris segment 16 such as a quadrant shown in FIG. 3. Calculating the centroid of the pie shaped quadrant follows the same formula above and only needs the iris edge 16 for that segment in order for this point to be calculated.

In summary the key feature of the present invention is the use of the iris edge 16 as a basis for establishing landmarks for eye tracking. The iris edge 16 may be used itself as a landmark or collection of landmarks in the form of a single iris edge point, as a single iris edge segment, as a collection of points or segments of the iris edge and combinations of iris edge points and iris edge segments. Further the iris edge 16 may be used to calculate an iris center point X, or other distinct point that is used as a landmark for eye tracking, and these can be used individually or in combination with each other. The landmarks that are calculated from the iris edge 16 may be used in combination with the landmarks formed by the iris edge 16 itself.

Further the iris based landmarks (which includes the landmarks formed by the iris itself) of the present invention can be used with known prior art landmarks to improve the prior art tracking methodologies. For example, the present invention can use both pupil center and iris based landmarks to track the eye 10 position. It is believed that the iris edge 16 based landmarks will provide for more precision in eye tracking methodologies and open up greater diagnostic possibilities accordingly.

Although the present invention has been described above by reference to an embodiment of the invention, the present invention is not limited to the embodiments described above. Modifications and variations of the embodiment described above will occur to those skilled in the art, in light of the above teachings without departing from the spirit of the present invention The present invention, therefore, to be limited only as indicated by the scope of the claims appended hereto and equivalents thereto.

What is claimed is:

1. A method of identifying at least one landmark in the eye comprising the steps of:
   digitizing an image of the eye;
   identifying at least a portion of the edge of the iris from the digitized image of the eye; and
   calculating a centroid of an area defined by the identified edge portion of the iris wherein the centroid forms at least one landmark in the eye.

2. The method of claim 1 further including the steps of calculating a geometric center of the iris based upon the identified edge of the iris, and wherein the step of calculating a geometric center of the iris includes identifying discontinuities of the identified iris edge and if any such discontinuities are found utilizing an iris edge approximation between the discontinuities to calculate the geometric center.

3. The method of identifying at least one landmark in the eye of claim 1 wherein the fixed landmarks based upon the identified portion of the edge of the iris are selected from the group of a single iris edge point, a single iris edge segment, a collection of iris edge points, a collection of iris edge segments, and combinations of iris edge points and iris edge segments.

4. The method of identifying at least one landmark in the eye of claim 1 wherein the fixed landmarks based upon the identified portion of the edge of the iris includes a centroid of a pie shaped quadrant defined by a segment of an identified segment portion of the edge of the iris.

5. The method of identifying at least one landmark in the eye of claim 1 wherein the fixed landmarks based upon the identified portion of the edge of the iris are selected from the group of a single iris edge segment, a collection of iris edge points, and a collection of iris edge segments.

6. A method of eye tracking comprising the steps of:
   digitizing an image of the eye;
   identifying at least a portion of the edge of the iris from the digitized image of the eye;
   establishing at least one fixed landmark based upon the identified portion of the edge of the iris; and
   tracking the movement of the at least one landmark over time.

7. The method of claim 6 further including the steps of calculating a geometric center of the iris based upon the identified edge of the iris, wherein the geometric center of the iris is one said landmark, and wherein the step of calculating a geometric center of the iris includes identifying discontinuities of the identified iris edge and if any such discontinuities are found utilizing an iris edge approximation between the discontinuities to calculate the geometric center.

8. The method of eye tracking of claim 6 further including the step of using both pupil center and iris based landmarks to track the eye position.

9. The method of eye tracking of claim 6 wherein the fixed landmarks based upon the identified portion of the edge of the iris are selected from the group of a single iris edge point, a single iris edge segment, a collection of iris edge points, a collection of iris edge segments, and combinations of iris edge points and iris edge segments.

10. The method of eye tracking of claim 6 wherein the fixed landmarks based upon the identified portion of the edge of the iris includes a centroid of a pie shaped quadrant defined by a segment of an identified segment portion of the edge of the iris.

11. The method of eye tracking of claim 6 further including the step of identifying small eye movements including micro-tremors from a review of the tracking of the movement of the at least one landmark over time.

12. The method of eye tracking of claim 11 further including the step of using measured eye movements as assessment of the state of consciousness.

13. The method of eye tracking of claim 11 further including the step of using measured eye movements as assessment or indication of brainstem death.

14. A method of assessing the state of consciousness of a subject comprising the steps of:
   digitizing an image of the eye;
   identifying at least a portion of the edge of the iris from the digitized image of the eye;
   establishing at least one fixed landmark based upon the identified portion of the edge of the iris;
   tracking the movement of the at least one landmark over time;
   identifying small eye movements including micro-tremors from a review of the tracking of the movement of the at least one landmark over time; and
   utilizing the tracked small eye movement in an assessment of the state of consciousness of a subject.

15. The method of assessing the state of consciousness of a subject of claim 14 further including the steps of calculating a geometric center of the iris based upon the identified edge of the iris, wherein the geometric center of the iris is one said landmark, and wherein the step of calculating a geometric center of the iris includes identifying discontinuities of the identified iris edge and if any such discontinuities are found utilizing an iris edge approximation between the discontinuities to calculate the geometric center.

16. The method of assessing the state of consciousness of a subject of claim 14 further including the step of using both pupil center and iris based landmarks to track the eye position.

17. The method of assessing the state of consciousness of a subject of claim 14 wherein the fixed landmarks based upon the identified portion of the edge of the iris are selected from the group of a single iris edge point, a single iris edge segment, a collection of iris edge points, a collection of iris edge segments, and combinations of iris edge points and iris edge segments.

18. The method of assessing the state of consciousness of a subject of claim 14 wherein the fixed landmarks based upon the identified portion of the edge of the iris includes a centroid of a pie shaped quadrant defined by a segment of an identified segment portion of the edge of the iris.

* * * * *